(12) United States Patent
Morgan et al.

(10) Patent No.: US 10,359,458 B2
(45) Date of Patent: Jul. 23, 2019

(54) SYSTEMS AND METHODS FOR AUTOMATED MAPPING AND ACCURACY-TESTING

(71) Applicant: COVIDIEN LP, Mansfield, MA (US)

(72) Inventors: Sean M. Morgan, Gloden Valley, MN (US); Keith E. Jasperson, Andover, MN (US); Michael R. Weisenberger, Minneapolis, MN (US)

(73) Assignee: COVIDIEN LP, Mansfield, MA (US)

( * ) Notice: Subject to any disclaimer, the term of this patent is extended or adjusted under 35 U.S.C. 154(b) by 120 days.

(21) Appl. No.: 15/240,635

(22) Filed: Aug. 18, 2016

(65) Prior Publication Data

US 2017/0097383 A1 Apr. 6, 2017

Related U.S. Application Data

(60) Provisional application No. 62/237,084, filed on Oct. 5, 2015.

(51) Int. Cl.
*A61B 34/20* (2016.01)
*G01R 29/08* (2006.01)
*A61B 17/00* (2006.01)

(52) U.S. Cl.
CPC .......... *G01R 29/0892* (2013.01); *A61B 34/20* (2016.02); *A61B 2017/00725* (2013.01); *A61B 2034/2051* (2016.02)

(58) Field of Classification Search
CPC .. A61B 2034/2051–2053; A61B 34/20; A61B 2034/2046–2053

(Continued)

(56) References Cited

U.S. PATENT DOCUMENTS 5,818,235 A 10/1998 Simonov et al.
5,923,174 A * 7/1999 Darling, Jr. ........ G01R 29/0814
324/637

(Continued)

FOREIGN PATENT DOCUMENTS

EP 2468208 A2 6/2012
JP H0958190 A 3/1997

(Continued)

OTHER PUBLICATIONS

Office Action for corresponding Japanese Application No. 2016-185604 dated Jul. 18, 2017.

(Continued)

*Primary Examiner* — Patrick Assouad
*Assistant Examiner* — Demetrius R Pretlow

(57) ABSTRACT

An apparatus for mapping and accuracy-testing an electromagnetic navigation system includes a sensor sensing electromagnetic vectors of an electromagnetic field, a carriage moving the sensor along a first direction and a second direction different from the first direction, a first position detector operatively associated with the sensor and detecting a first position of the sensor along the first direction, a second position detector operatively associated with the sensor and detecting a second position of the sensor along the second direction, and a controller operatively associated with the sensor and controlling movements of the carriage along the first and second directions and mapping the electromagnetic field based on the sensed electromagnetic vectors at predetermined positions in a coordinate system defined by the first direction, the second direction, and a third direction perpendicular to a plane defined by the first and second directions.

16 Claims, 11 Drawing Sheets

(58) Field of Classification Search
USPC .................................. 324/219, 207.11–207.12
See application file for complete search history.

(56) References Cited

U.S. PATENT DOCUMENTS

| | | | |
|---|---|---|---|
| 6,377,041 B1 | 4/2002 | Jones, Jr. et al. | |
| 6,636,757 B1 | 10/2003 | Jascob et al. | |
| 6,822,443 B1 | 11/2004 | Dogaru | |
| 7,043,848 B2 | 5/2006 | Hollman et al. | |
| 7,085,400 B1 | 8/2006 | Holsing et al. | |
| 7,397,266 B2 | 7/2008 | Pommerenke | |
| 7,933,641 B2 * | 4/2011 | Maschke | A61B 6/4441 600/424 |
| 8,143,903 B2 | 3/2012 | Pommerenke et al. | |
| 9,599,740 B2 * | 3/2017 | Olsson | G01V 3/08 |
| 9,703,002 B1 * | 7/2017 | Olsson | H01M 2/105 |
| 9,867,588 B2 * | 1/2018 | Amiri | A61B 6/547 |
| 9,921,185 B2 * | 3/2018 | Freear | G01N 27/82 |
| 2006/0232259 A1 * | 10/2006 | Olsson | G01R 29/0871 324/67 |
| 2008/0079421 A1 | 4/2008 | Jensen | |
| 2009/0295405 A1 | 12/2009 | Pommerenke et al. | |
| 2010/0168556 A1 | 7/2010 | Shen et al. | |
| 2013/0082680 A1 | 4/2013 | Wu et al. | |
| 2014/0354300 A1 | 12/2014 | Ramachandran et al. | |
| 2017/0151022 A1 * | 6/2017 | Jascob | A61B 34/20 |
| 2017/0365055 A1 * | 12/2017 | Mintz | A61B 1/00147 |

FOREIGN PATENT DOCUMENTS

| | | | |
|---|---|---|---|
| JP | 2000214198 A | 8/2000 | |
| JP | 2001183434 A | 7/2001 | |
| JP | 2010190709 A | 9/2010 | |
| JP | 2012-130703 A | 7/2012 | |
| WO | 2015/145300 A2 | 10/2015 | |

OTHER PUBLICATIONS

Alfred M. Franz, et al., Electromagnetic Tracking in Medicine—A Review of Technology, Validation, and Applications, IEEE Transactions on Medical Imaging, vol. 33, No. 8, Aug. 1, 2014, pp. 1702-1725.

Christopher Nafis, et al., Method for estimating dynamic EM tracking accuracy of Surgical Navigation tools, SPIE—International Society for Optical Engineering. Proceedings, vol. 6141, Mar. 2, 2006,18 pages.

Joe Kulesza, et al., Portable Magnetic Measurement System, Proceedings of EPAC08, Genoa, Italy, WEPC108, Jul. 17, 2008, 3 pages.

European Search Report in corresponding EP Application No. 16191030.2 dated Feb. 24, 2017, 9 pages.

Examination Report for corresponding Australian Application No. 2016219564 dated Sep. 1, 2017.

Canadian Office Action dated Nov. 8, 2017 in corresponding Canadian Patent Application No. 2,940,792, 6 pages.

Japanese Office Action dated May 1, 2018 and issued in corresponding Japanese Patent Application No. 2016-185604, with English translation.

First Office Action issued by the State Intellectual Property Office of the People's Republic of China dated Nov. 1, 2018 in corresponding Chinese Patent Application No. 201610858648.1 with English translation.

Japanese Notice of Allowance dated Nov. 2, 2018 in corresponding Japanese Patent Application No. 2016-185604 with English translation.

* cited by examiner

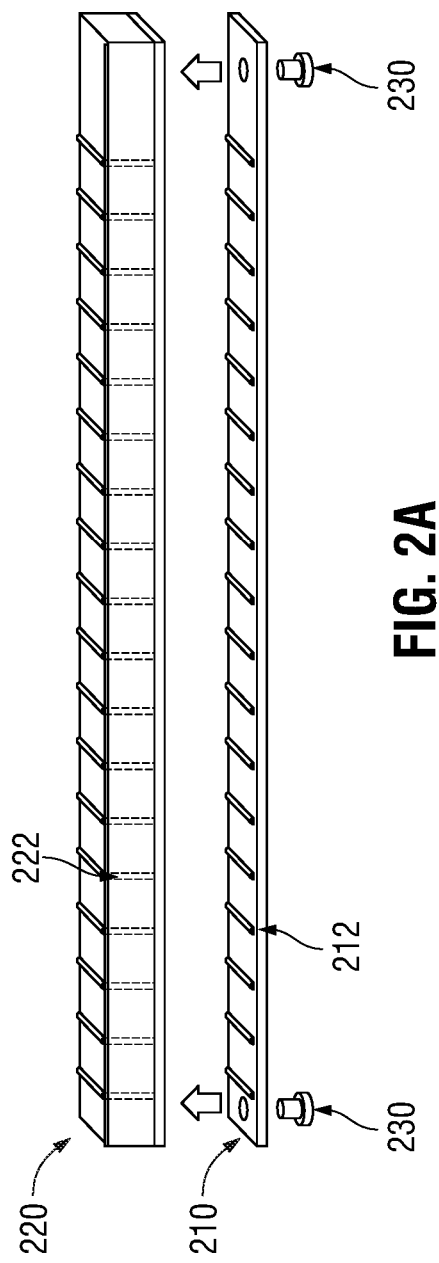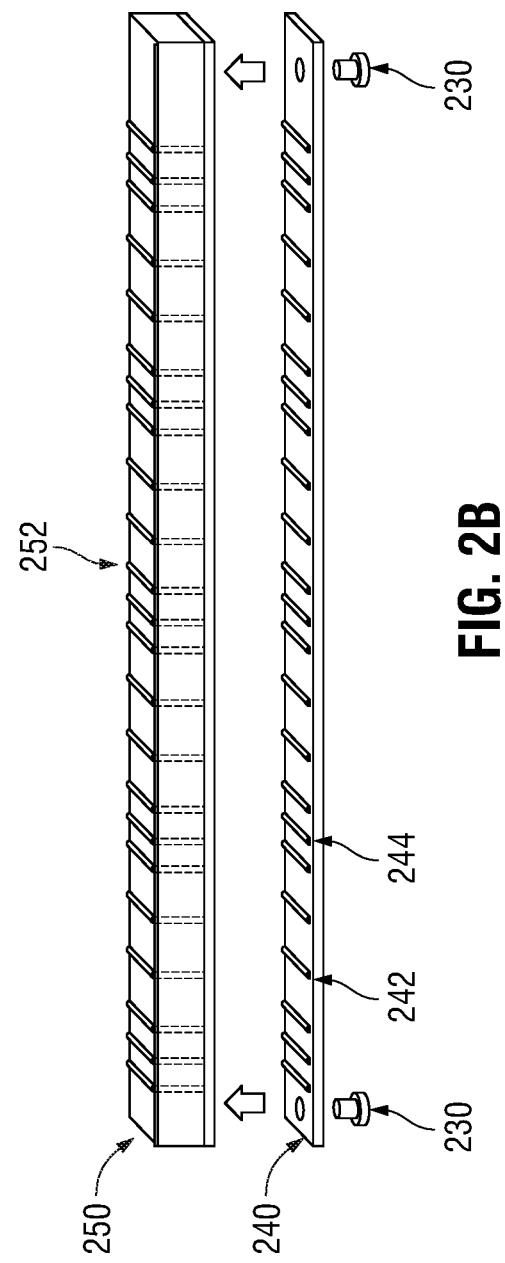

SYSTEMS AND METHODS FOR AUTOMATED MAPPING AND ACCURACY-TESTING

CROSS REFERENCE TO RELATED APPLICATION

The present application claims the benefit of and priority to U.S. Provisional Application Ser. No. 62/237,084, filed on Oct. 5, 2015, the entire contents of which are incorporated herein by reference.

BACKGROUND

Technical Field

The present disclosure relates to systems and methods for automated mapping and accuracy-testing for electromagnetic navigation systems. More particularly, the present disclosure relates to systems and methods that automatically measure strength of the electromagnetic fields for electromagnetic navigation to obtain mapping data and test accuracy of the mapping data.

Discussion of Related Art

Electromagnetic navigation (EMN) systems have helped to expand potentials of treatment to internal organs and diagnosis of diseases. The EMN systems rely on non-invasive imaging technologies, such as computed tomography (CT) scanning, magnetic resonance imaging (MRI), or fluoroscopic technologies. These images may be registered to a patient within electromagnetic fields, and as a result the location of a sensor placed inside of the patient within the electromagnetic fields can be identified in the images. As a result, the EMN in combination with these non-invasive imaging technologies is used to identify a location of a target and to help clinicians navigate inside of the patient's body to the target.

In order to visualize internal organs and diagnose diseases, accurate mapping data needs to be stored in the EMN system. Generally, the EMN systems measure strength of EM fields, compare the measured strength with the mapping data, and generate visual images. The more accurate the mapping data, the more accurate images can be obtained and the more accurate locations of targets or internal organs can be identified. The mapping data has been obtained manually. For example, manufacturers or users manually measure strength of EM field at each of the predetermined position and store the measured strength as the mapping data into EMN systems before initially using the EMN systems. Accuracy of the mapping data can be enhanced by automation of generating the mapping data.

Physical structures of an EMN system may be changed while installing the EMN system at an operating room different from the place of generating the mapping data and/or after the EMN system has been used for a period. Further, EM fields generated by the EMN system may be influenced by an external ferrous material near the system and generated images can neither accurately depict internal organs or targets nor can be used to diagnose diseases. Thus, automatic accuracy tests of the mapping data can also improve assurance of accuracy of the mapping data.

SUMMARY

Generally, the present disclosure provides systems and methods for automatically generating mapping data for EMN systems and testing accuracy of the mapping data. In an embodiment, the apparatus includes a sensor sensing EM vectors of an EM field generated by the EMN system, a carriage moving the sensor along a first direction and a second direction different from the first direction, wherein the sensor is fixedly attached to the carriage, a first position detector operatively associated with the sensor and detecting a first position of the sensor along the first direction, where the first position is one of predetermined positions along the first direction, a second position detector operatively associated with the sensor and detecting a second position of the sensor along the second direction, wherein the second position is one of predetermined positions along the second direction, and a controller operatively associated with the sensor and controlling movements of the carriage along the first and second directions and mapping the EM field based on the sensed EM vectors at predetermined positions in a coordinate system defined by the first direction, the second direction, and a third direction perpendicular to a plane defined by the first and second directions.

In an aspect, the apparatus further includes a plurality of signal generators each of which being configured to generate a signal and each of which being positioned at a corresponding position of the predetermined positions along the first direction. The sensor is configured to sense an EM vector when the first position detector detects a signal strength generated by each of the plurality of signal generators along the first direction. The plurality of signal generators are light emitting diodes (LEDs) where the first position detector detects a strength of light emitted by the LEDs. The plurality of signal generators along the second direction is activated for mapping and accuracy-testing.

In another aspect, the predetermined positions along the second direction include a first group and a second group, where the sensor is configured to sense an EM vector for mapping at the first group of the predetermined positions along the second direction. The sensor is configured to sense an EM vector for accuracy-testing at the second group of the predetermined positions along the second direction. The apparatus further includes a first plurality of signal generators each being configured to generate a signal, and each of which is positioned at a corresponding position of the first group and a second plurality of signal generators each being configured to generate a signal, and each of which is positioned at a corresponding position of the second group.

The sensor is configured to sense an EM vector when the second position detector detects a maximum strength of a signal generated by one of the first and second pluralities of signal generators along the second direction. The first and second pluralities of signal generators are light emitting diodes (LEDs), and wherein the second position detector detects strength of light emitted by the LEDs. The LEDs of the first plurality of signal generators are configured to generate light having a first color, and wherein LEDs of the second plurality of signal generators are configured to generate light having a second color different from the first color.

In another aspect, each of the first and second position detectors defines a slit therein, and the first and second position detectors are configured to detect strength of light passing through the corresponding slit of the first and second position detectors, respectively.

The first plurality of signal generators are activated and the second plurality of signal generators are deactivated when the apparatus is operated for generating mapping data. The first plurality of signal generators are deactivated and the second plurality of signal generators are activated when the apparatus is operated for generating accuracy-testing data.

In yet another aspect, the sensor includes an EM sensor configured to sense an EM vector along the third direction, and wherein the EM sensor is configured to be manually moved along the third direction. The EM sensor is configured to sense 6 degrees of freedom.

In yet another aspect, the sensor includes a plurality of sensors, each of which is located at corresponding one of predetermined positions along the third direction.

In still another aspect, the apparatus further includes a bottom layer configured to center the apparatus over an EM field generated by the EMN system.

In still another aspect, the apparatus is mostly made of non-ferrous materials.

In yet another aspect, the apparatus further includes a first motor coupled with the sensor via a first shaft and configured to move the sensor along the first direction, and a second motor coupled with the sensor via a second shaft and configured to move the sensor along the second direction. The first and second motors are spaced a distance from the EM field a sufficient distance to minimize influence to the EM field and are non-ferrous. The controller is further configured to control the first and second motors.

In another embodiment, a method for mapping and accuracy-testing an EM field generated by an EMN system includes moving a sensor to an initial position on a plane defined by a first direction and a second direction different from the first direction, sensing an EM vector at each of predetermined positions in a coordinate system defined by the plane and a third direction perpendicular to the plane, sampling the sensed EM vector to obtain digital samples, and generating data for mapping or accuracy-testing based on the digital samples.

The predetermined positions are defined by first predetermined positions along the first direction, second predetermined positions along the second direction, and third predetermined positions along the third direction. The second predetermined position includes a first group of positions for mapping and a second group of positions for accuracy-testing, wherein signal generators located at the first group are configured to generate signals for mapping, and further wherein signal generators located at the second group are configured to generate signals for accuracy-testing.

A signal generator is located at each of the third predetermined positions and the method further includes moving the sensor along the third direction and sensing an EM vector when strength of a signal generated by a signal generator is a maximum.

In an aspect, the sensor includes EM sensors, each of which is located at a corresponding position of the third predetermined positions.

In another aspect, the step of moving the sensor to the initial position includes activating a first signal generator located at a beginning position of the first predetermined positions and a second signal generator located at a beginning position of the second predetermined positions, and moving the sensor to a position where the sensed strength is a maximum along the first and second directions. The step of moving the sensor further includes deactivating all of signal generators except the first and second signal generators.

In another aspect, the method further includes generating a fitted curve of the mapping data based on the digital samples and storing the fitted curve in the EMN system. Further, the method includes generating accuracy-testing data, calculating deviation of the accuracy-testing data from the fitted curve, determining whether the deviation is greater than a threshold, and generating a warning of re-generating the mapping data when it is determined that the deviation is not less than the threshold. The method further includes disabling the EMN system when it is determined that a deviation is not less than a threshold.

Any of the above aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which:

FIGS. 2A and 2B are perspective views of Z-axis and X-axis rails with corresponding printed circuit boards of the system of FIG. 1, respectively, in accordance with an illustrative embodiment of the present disclosure;

DETAILED DESCRIPTION

The present disclosure is related to systems and methods for automatically generating mapping data for EMN systems and testing accuracy of the mapping data. Before using an EMN system, the present disclosure provides systems and methods to measure strength of EM field at predetermined positions over an EM field generated by the EMN system, generate mapping data based on the measured strength, and store the mapping data into the EMN system. Further, the systems and methods of the present disclosure test the accuracy of the mapping data of the EMN system after a period of usage of the EMN system and re-generate new mapping data when deviation of the test from the mapping data is greater than a predetermined threshold value.

Although the present disclosure will be described in terms of specific illustrative embodiments, it will be readily apparent to those skilled in this art that various modifications, rearrangements, and substitutions may be made without departing from the spirit of the present disclosure. The scope of the present disclosure is defined by the claims appended to this disclosure.

Figure 1:
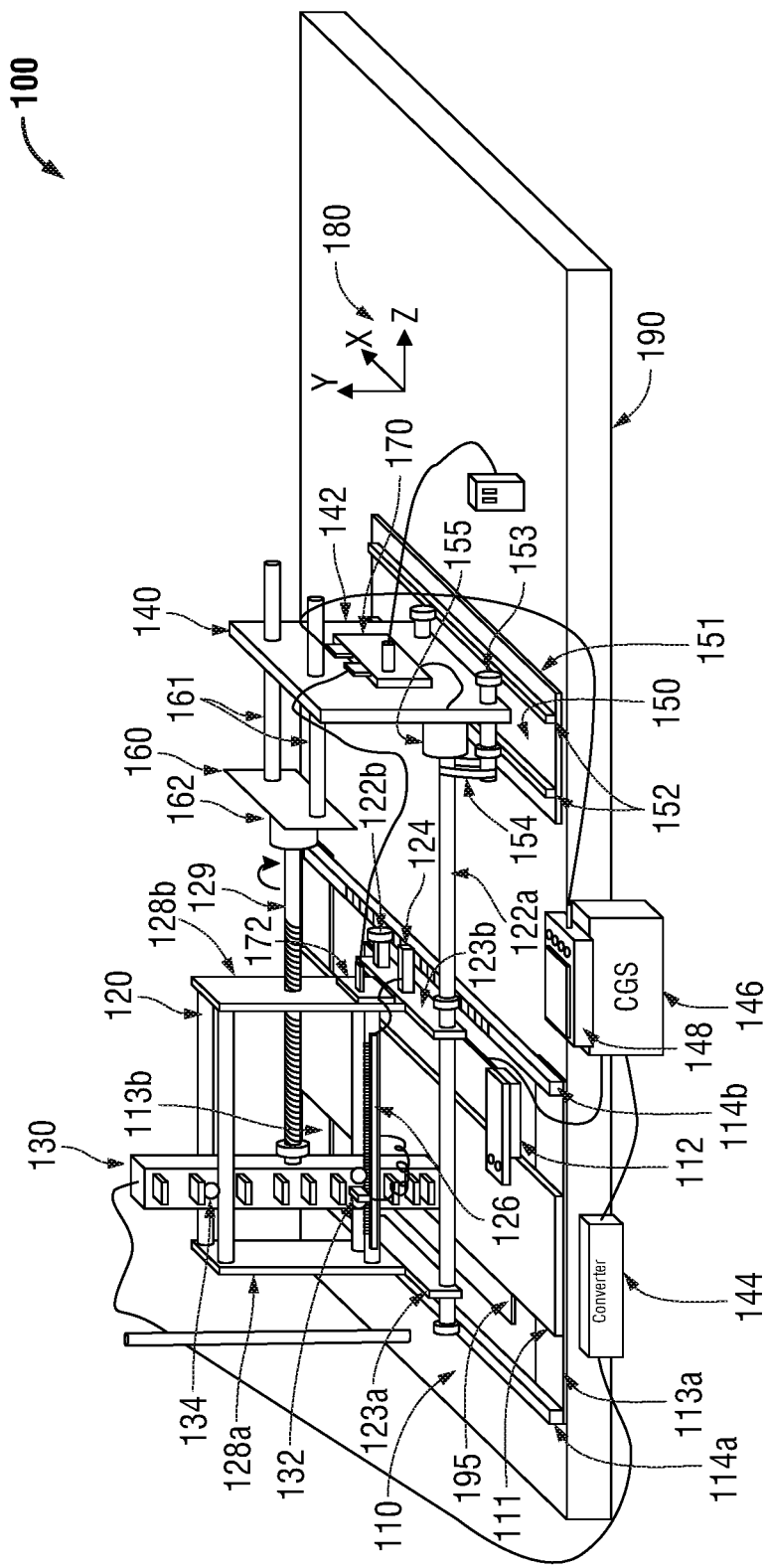
FIG. 1 is a perspective view of a system for generating mapping data and testing accuracy of the mapping data for an electromagnetic navigation (EMN) system in accordance with an illustrative embodiment of the present disclosure.

FIG. 1 illustrates a system 100 for automatically generating mapping data for an electromagnetic navigation (EMN) system and testing accuracy of the mapping data. For example, an EMN system may be the ELECTROMAGNETIC NAVIGATION BRONCHOSCOPY® system currently sold by Covidien LP, a division of Medtronic plc. The EMN system utilizes electromagnetic field to non-invasively identify locations of internal organs and diseased portions inside of a patient's body. Strength of electromagnetic field specific to a predetermined position is used to identify a location of such and is saved in the EMN system in a form of mapping data, which the system 100 generates.

The system 100 includes a platform 110, a carriage 120, a field sensing device 130, and a controller 140. The platform 110 is placed on a location board 190 of an EMN system. In particular, the platform 110 stands over an EM field generator 195 of the EMN system. The platform 110 includes a corner piece 112, which frames the location board 190 so that the system 100 may be centered over the EM field generated by the EM field generator 195. In an aspect, the corner piece 112 may be two corner pieces which are diagonally positioned so that the two corner pieces fit two diagonal corners of the EM field generator 195.

The carriage 120 includes two rails 114a and 114b aligned in parallel along the X-axis as shown in an axis-indicator 180 placed on the platform 110 and supporting the rest of the carriage 120. The first rail 114a is just a rail while the second rail 114b may be formed of a composite of a printed circuit board (PCB) 210 and a riding surface 220, as shown in FIG. 2A. The PCB 210 includes a plurality of grid position signal source generators 212, which generate signals for indicating predetermined positions for mapping data for EMN systems.

In an aspect, the grid position signal source generators 212 may be light emitting diodes (LEDs), laser light generators, audio generators, and the like. In another aspect, the grid position signal source generators 212 are located on predetermined positions on the PCB 210. In instances where the grid position signal source generators 212 are LEDs, the riding surface 220 may be sufficiently transparent to transmit the light generated by the grid position signal source generators 212 through the riding surface 220. The transparency of the riding surface 220 does not substantially disperse the light but directs the light to the top of the riding surface 220. In another aspect, the riding surface 220 may have slits 222 located over the grid position signal source generators 212 so that the light generated by the grid position signal source generators 212 are substantially unobstructed to transmits through the riding surface 220. The riding surface 220 may be affixed to the PCB 210 via a fixing means 230, which includes a rivet, adhesive, nail, staples, or the like.

The platform 110 may also include pieces that connect each element of the platform 110. For example, a center piece 111 may be used to hold the corner piece 112 and two bottom pieces 113a and 113b are used to connect the two rails 114a and 114b, and the center piece 111, as shown in FIG. 1. Further, the platform 110 is used as a base for holding the carriage 120.

The carriage 120 includes first and second shafts 122a and 122b, which are parallelly positioned to each other along Z-axis as shown in the axis-indicator 180, and first and second side bars 123a and 123b. Each of the first and second shafts 122a and 122b has two wheels rolling over the two rails 114 and 114b, respectively. Two wheels may be made of rubber or similar materials. The first shaft 122a is mechanically coupled to the controller 140 so that the carriage 120 can move along the X-axis over the two rails 114 and 114b. The first and second shafts 122a and 122b are locked by the first and second side bars 123a and 123b.

A signal detector 124 may be attached to the second side bar 123b and positioned over the second rail 114b. When the first and second shafts 122a and 122b are moved along the X-axis, the signal detector 124 senses strength of the signals generated by the grid position signal source generators 212 of FIG. 2A. In an aspect, the signal detector 124 may comprise a slit formed on its underside to sense strength of the signal from a grid position signal source generators 212 which the signal detector passing over. Sensed result is transmitted to the controller 140.

The carriage 120 further includes a third rail 126 extending along the Z-axis direction as shown in the axis-indicator 180. The third rail 126 is formed of a composite including a printed circuit board (PCB) 240 and a riding surface 250, as shown in FIG. 2B. The PCB 240 includes a plurality of grid position signal source generators, which are separated into two groups, i.e., a first kind 242 and a second kind 244. The grid position signal source generators of the first kind 242 generate signals for generating mapping data and the grid position signal source generators of the second kind 244 generate signals for testing accuracy of the mapping data.

In an aspect, the grid position signal source generators 242 and 244 may be LEDs, laser light generators, audio generators, and the like. In another aspect, the grid position signal source generators 242 and 244 are located at predetermined positions on the PCB 240. In further aspect, each grid position signal source generator of the second kind 244 is positioned between two consecutive grid position signal source generators of the first kind 242. In still further aspect, the number of grid position signal source generators of the first kind 242 is greater than that of the second kind 244. In yet another aspect, grid position signal source generators of the first kind 242 may be positioned and equally distanced from each other. Nevertheless, the positions of the grid position signal source generators 242 and 244 are not limited to these aspects but can be modified by one having ordinary skill in the art without departing from the scope of the present disclosure.

In case that the grid position signal source generators 242 and 244 are LEDs, the riding surface 250 may be sufficiently transparent to transmit the light generated by the grid position signal source generators 242 and 244 to the top of the riding surface 250. The transparency of the riding surface 250 does not disperse the light substantially but directs the light through the top surface of the riding surface 250. In an aspect, the riding surface 250 may have slits 252 located over the grid position signal source generators 242 and 244 so that the light generated by the grid position signal source generators 242 and 244 can be unobstructed and transmitted through the riding surface 250.

The grid position signal source generators of the first kind 242 may generate a first color and the grid position signal source generator of the second kind 244 may generate a second color different from the first color. For example, the first color may be green and the second color may be red. In an aspect, a same color may be generated by the grid position signal source generators 242 and 244. The bottom surface of the riding surface 250 may be affixed with the PCB 240 via a fixing means 260, which includes a rivet, adhesive, nail, staples, or the like.

The carriage 120 also includes first and second vertical bars 128a and 128b, which are affixed over the first and second sidebars 123a and 123b, respectively. The first and second vertical bars 128a and 128b are distanced and connected by sidebars and the third rail 126.

The carriage 120 also includes a third shaft 129, which connects the field sensing device 130 to the controller 140 through the second vertical bar 128b. The third shaft 129 may have circular gear teeth thereon or another means that mechanically and operationally couples to an opening in the second vertical bar 128b, so that rotation of the third shaft 129 around Z-axis can be converted into a linear directional movement of the field sensing device 130 along the Z-axis but does not affect movement of the carriage 120. Structure of the opening of the second vertical bar 128b may be readily implemented by a person having ordinary skill in the art.

The field sensing device 130 includes a signal detector 132 and a plurality of sensors 134. The signal detector 132 is positioned over the third rail 126 and senses strength of the signals generated by the grid position signal source generators of the first kind 242 and the second kind 244. In an aspect, the signal detector 132 may also include a slit 252 formed on its underside to detect strength of the signal passing through the slit 252.

The plurality of sensors 134 are located at predetermined positions along the Y-axis and configured to detect EM vectors of the EM field generated by the EM field generator 195 of the EMN system. In an aspect, the plurality of sensors 134 may be 6 degrees of freedom (DOF) sensors, which can sense three directions (e.g., X-, Y-, and Z-directions) and three rotations (e.g., pitch, yaw, and roll) based on sensed EM vectors of the EM fields. The 6 DOF sensors is provided as an example and not intended to limit other kinds of sensors for the plurality of sensors 134.

The controller 140 includes a vertical board 142, a first motor portion 150, a second motor portion 160, and a control circuitry 170. The first motor portion 150 is attached to the vertical board 142. The first motor portion 150 is connected to the first shaft 122a of the carriage 120 and configured to control directional movements of the carriage 120 along the X-axis. The second motor portion 160 is connected to the third shaft 129 of the carriage 120 and configured to control directional movements of the field sensing device 130 along the Z-axis. Since the control circuitry 170 is connected with an interconnect PCB 172 configured to relay information (position or orientation data) between the control circuitry 170 and the signal detectors 124 and 132, the control circuitry 170 controls the movements of the carriage 120 and the field sensing device 130 along the X-axis and Z-axis, respectively and independently, based on the position or orientation data.

The first motor portion 150 includes a bottom 151, two rails 152, two shafts 153, a belt 154, and a first motor 155. The bottom 151 forms the base of the controller 140 and two rails 152 are affixed in parallel to the top surface of the bottom 151 along the X-axis. Each of two shafts 153 includes two wheels configured to roll over the two rails 152, and is connected through the vertical board 142. When powered and controlled, the first motor 155 generates rotational movements, which is transmitted to the first shaft 122a. Then, the circular movements of the first shaft 122a cause the four wheels of the carriage 120 to roll over the two rails 114a and 114b.

One of the two shafts 153 is connected to the first motor 155 or the first shaft 122a via the belt 154 so that the four wheels of the first motor portion 150 also roll over the two rails 152 synchronously with the four wheels of the carriage 120. In this way, the controller 140 simultaneously follows movements of the carriage 120, correspondingly.

The second motor portion 160 includes one or more shafts 161 and a second motor 162. The shafts 161 connect the second motor 162 through openings of the vertical board 142 of the controller 140. When powered and controlled, the second motor 162 generates rotational movements around the Z-axis, which is transmitted to the third shaft 129. The rotational movements of the third shaft 129 around the Z-axis are converted to the directional movements along the Z-axis so that the field sensing device 130 moves along the Z-axis. The second motor 162 and the shafts 161 also move along the Z-axis corresponding to the movements of the field sensing device 130. The shafts 161 are configured to smoothly slide through an opening of the vertical board 142.

The first motor 155 and the second motor 162 are independently controlled by the control circuitry 170.

The controller 140 further includes a converter 144, a continuous guidance system (CGS) 146, and a computing device 148. The converter 144 is configured to receive sensed EM vectors from the field sensing device 130, which are analog signals, and to convert the analog result into digital samples. In one example, the sampling frequency of the converter 144 is an integer multiple of the frequency of the EM field generated by the EM field generator 195. The digital samples also include time stamp information indicating what time the plurality of sensors 134 senses the EM vectors.

The digital samples are transmitted to the CGS 146, which collects the magnetic field measurement data and computes the sensor locations and orientations for each coil within the EM sensor assembly. The magnetic field map that is generated from this data collection corrects for field distortions from ferrous objects in the environment. This map is used to accurately locate the EM sensors during the EMN procedures.

The CGS 146 sends digital samples, (i.e., sensor position and orientation samples) with the corresponding time stamp information to the computing device 148, which extracts mapping data from the digital samples. The control circuitry 170 sends positional information of the plurality of sensors 134 to the computing device 148. The computing device 148 associates the digital samples with the positional information and saves the results as mapping data.

Figure 3:
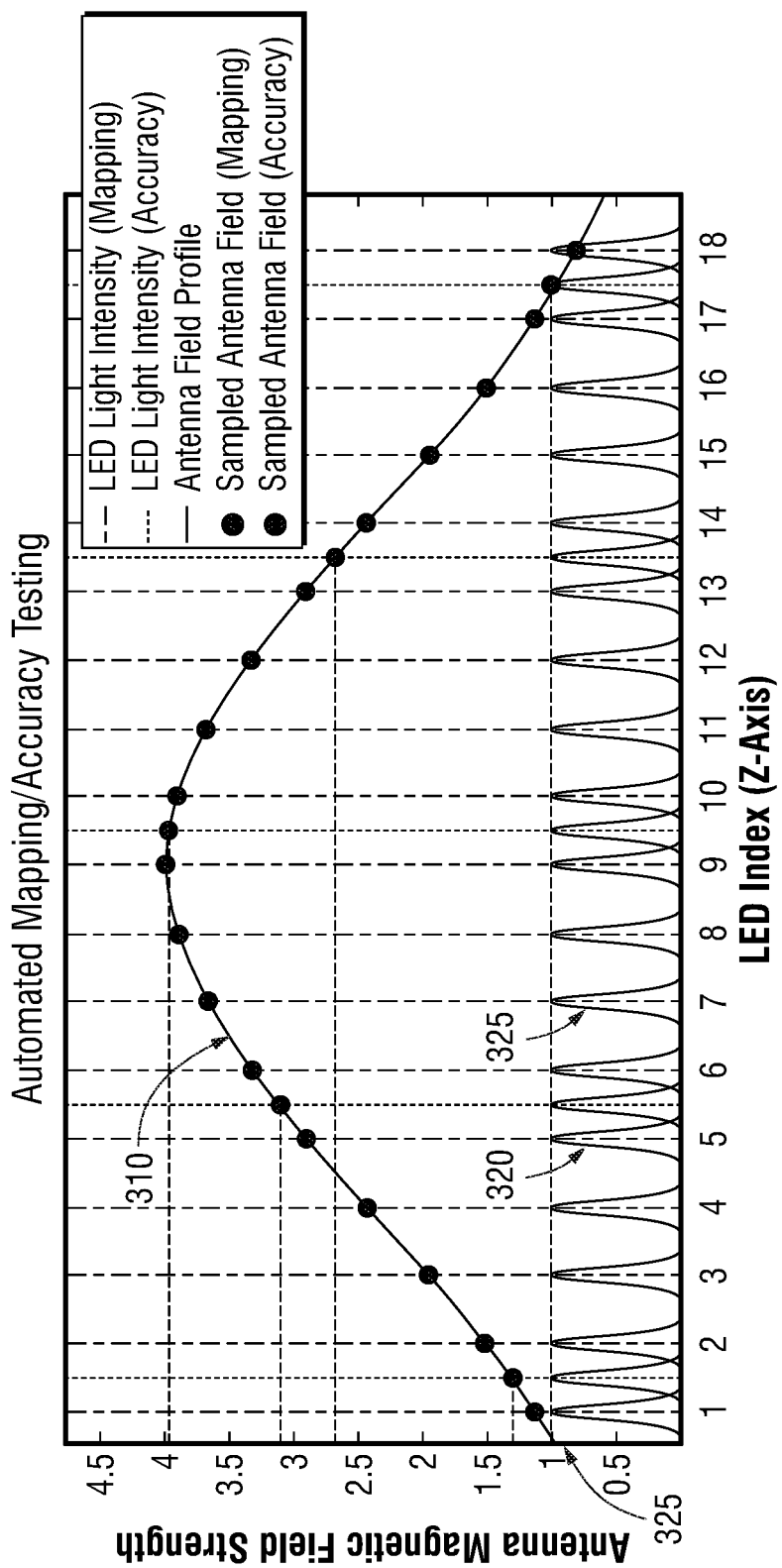
FIG. 3 is a graphical illustration of signal strength of mapping data along Z-axis in accordance with an illustrative embodiment of the present disclosure.
Figure 4:
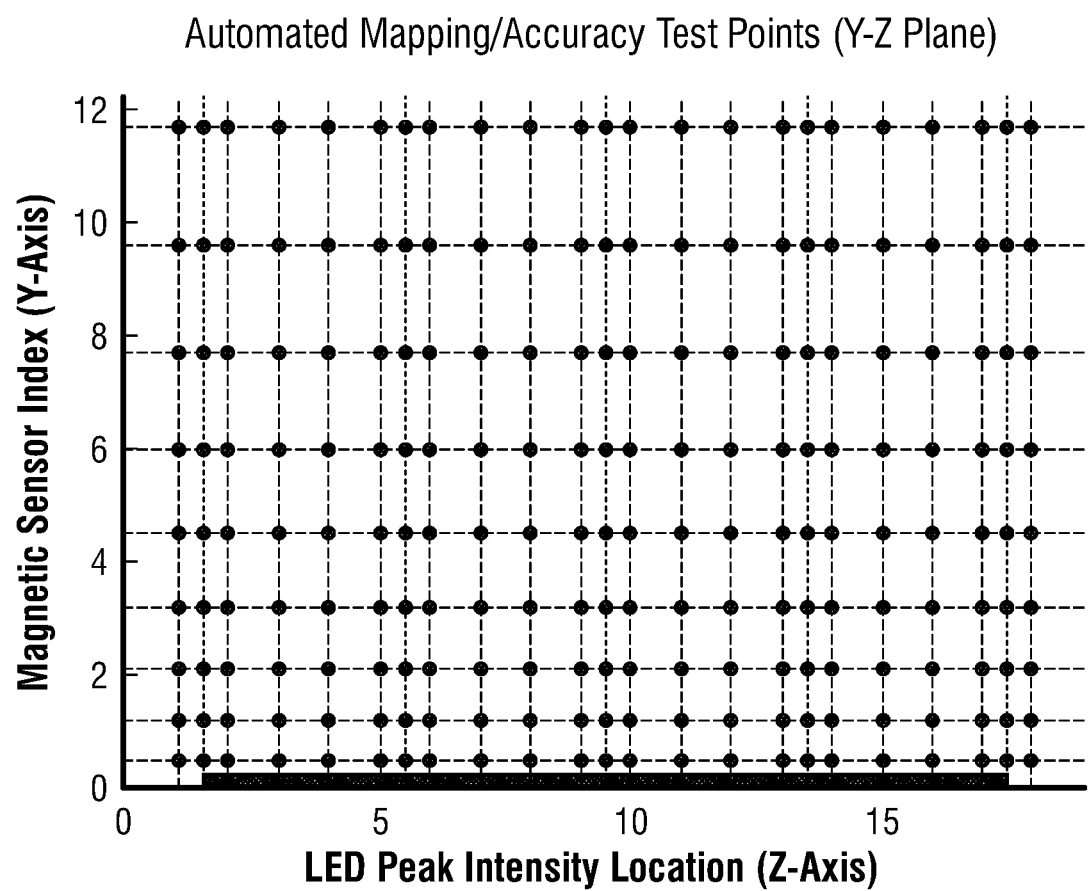
FIG. 4 is a graphical illustration of predetermined points in Y-Z plane in accordance with an illustrative embodiment of the present disclosure.

In an aspect, the computing device 148 further performs curve fitting process to calculate and find out fitted curves of the mapping data. FIG. 3 illustrates a fitted curve 310 based on mapping data of a position y at the Y-axis and a position x at the X-axis along the Z-axis. 18 predetermined positions for mapping data are illustrated as integer coordinates, such as 1-18, and 5 predetermined positions for accuracy testing data are illustrated in between coordinates 1 and 2, 5 and 6, 9 and 10, 13 and 14, and 17 and 18. The numbers of the predetermined positions for mapping data and for accuracy testing data are provided as examples and not intended limiting.

The computing device 148 utilizes curve fitting techniques to find a curve fitting to the 18 mapping data. The fitted curve 310 may be polynomial function based or harmonic function based. In an aspect, the first or last predetermined position may not be used for mapping data or accuracy testing data and may be used to indicate starting and ending positions to get data.

When generating the mapping data, the signal detector 124 of the carriage 120 senses strength of the signal generated by the grid position signal source generators of the first kind 242 through a slit. Curve 320 illustrates a distribution of the strength detected by the signal detector 124. When the strength reaches the maximum 325, the plurality of sensors 134 of the field sensing device 130 senses EM vectors of the EM field and transmits the sensed results to the converter 144 together with the time stamp information. After collecting mapping data for all predetermined positions for mapping data are obtained, the computing device 148 generates fitted curves.

Accuracy of the mapping data may be checked after the mapping data has been generated. In case of checking accuracy, the signal detector 124 of the carriage 120 senses strength of the signal generated by the grid position signal source generators of the second kind 244 through the slit 252. When the strength of the signal generated by the grid position signal source generators of the second kind 244 reaches the maximum 325, the plurality of sensors 134 of the field sensing device 130 senses EM vectors of the EM field and transmits the sensed results to the converter 144. The field sensing device 130 sends time stamp information with the sensed results. The time stamp information indicates when the EM vectors are sensed.

After the accuracy testing data is generated, a deviation error of the accuracy testing data from the fitted curve 310 is calculated. The fitted curve 310 provides expected strength at a predetermined position for accuracy testing, which is compared with the accuracy testing data obtained at the predetermined position. The computing device 148 determines whether the deviation error is within a tolerance range. In case when it is determined that the deviation error is not within the tolerance range, the operator or user of the system 100 is notified that the mapping data needs to be re-generated via displaying a warning message on a display screen or generating an warning audio.

As shown in FIGS. 2A-4, the grid position signal source generators of the second kind 244 are located on the Z-axis but not on the X-axis and not on the Y-axis. Thus, when the field sensing device 130 scans through the Z-axis, the field sensing device 130 senses the EM vectors at the predetermined positions based on the mode (i.e., generating mapping data or generating accuracy testing data) of the system 100. In other words, when the mode is set to generate mapping data, all data sensed by the field sensing device 130 is used to generate the mapping data when the signal detector 124 detects the maximum signal strength over a grid position signal source generator of the first kind 242 and all data sensed by the field sensing device 130 is not used for generating mapping data when the signal detector 124 detects the maximum signal strength at a grid position signal source generator of the second kind 244.

Figure 5:
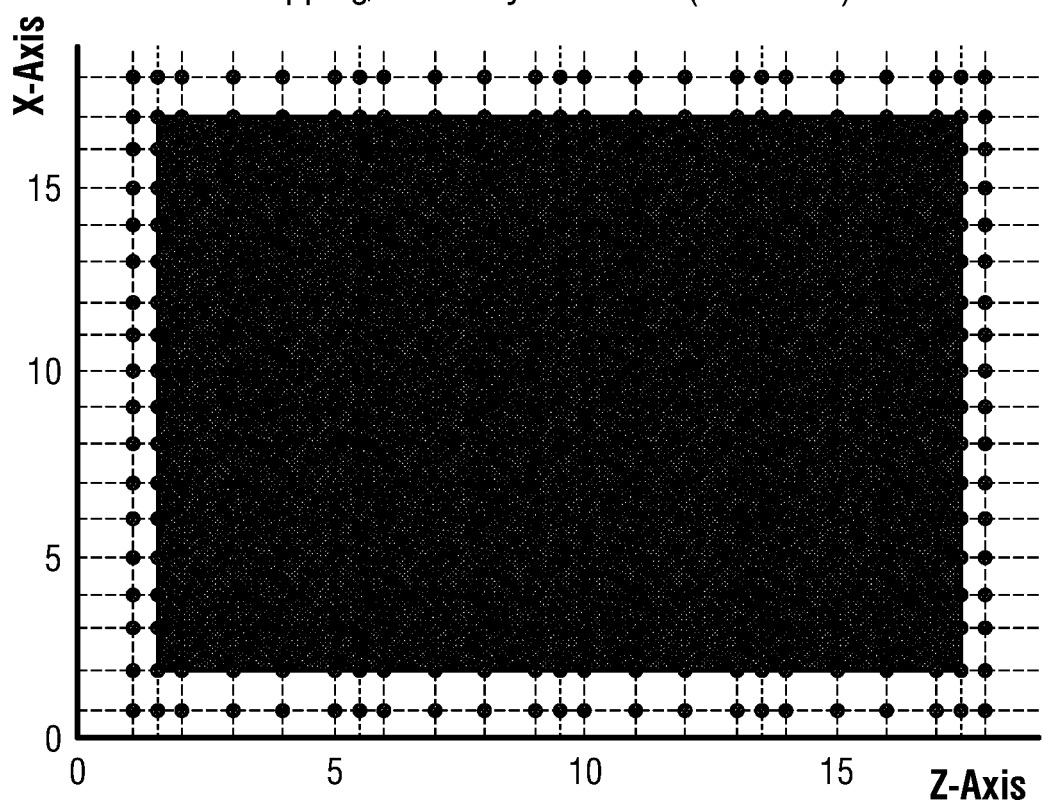
FIG. 5 is a graphical illustration of test points in X-Z plane in accordance with an illustrative embodiment of the present disclosure.

FIG. 5 illustrates predetermined positions in the X-Z plane. The field sensing device 130 senses the EM vectors from the first position to the last position along the X-axis likewise the field sensing device 130 senses the EM vectors from the first position to the last position along the Z-axis. In an aspect, the first and last position along the X-axis or the Z-axis may be used to initialize the position of the mapping data or the accuracy testing data. In other words, the first and last position may not be used for the mapping data or the accuracy testing data but used for the field sensing device 130 to start or end sensing EM vectors. As such, grayed area surround by the first and last positions may be used as the predetermined positions for generating mapping data and accuracy-testing data.

With regard to the initialization of the position, when a grid position signal source generator at the first or last position is powered on, the other grid position signal source generators may be powered down and the signal detector moves until the initialization light is found. As such, the position for initialization may be identified. In an aspect, after the position for initialization is found, the other grid position signal source generators are powered on and the field sensing device 130 starts sensing the EM vectors at predetermined positions where the grid position signal source generators emit light.

Figure 6:
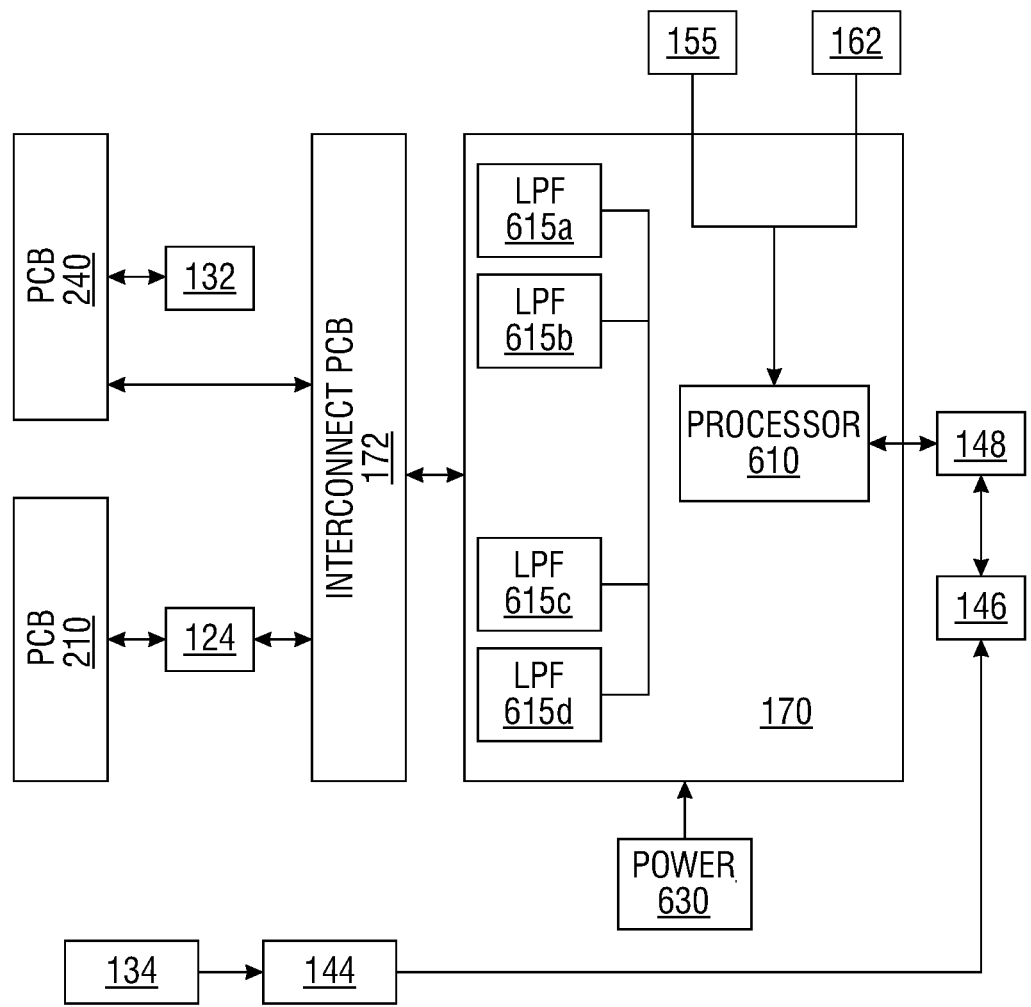
FIG. 6 is a functional block diagram of the system of FIG. 1 in accordance with an illustrative embodiment of the present disclosure.

FIG. 6 illustrates a functional block diagram of the system 100 of FIG. 1. The system 100 includes the control circuitry 170, which includes a processor 610 and low-pass filters (LPFs) 615a-615d. The control circuitry 170 controls the first motor 155 and the second motor 162. The control circuitry 170 is connected with an interconnect PCB 172 configured to relay information between the control circuitry 170 and the signal detectors 124 and 132.

When the control circuitry 170 is powered up from the power source 630, the processor 610 controls the first motor 155 and the second motor 162 so that the carriage 120 and the field sensing device 130 move to their initial position. The control circuitry 170 may activate all signals of the first or second grid position signal source generator at once. The first motor 155 and the second motor 162 may place the apparatus in a reset position along X-axis and Z-axis and then move to the first signal source along X-axis and Z-axis, separately. In an aspect, the control circuitry 170 may send a control signal to the PCB 210 to activate only the first grid position signal source generator 212 along the X-axis and to the PCB 240 to activate only the first grid position signal source generator along the Z-axis.

The signal detector 124 detects the signal generated by the grid position signal source generator 212. When the signal detector 124 detects the maximum strength of the signal, it sends a control signal to the interconnect PCB 172, which relays the control signal to the processor 610. The processor 610 controls and stops the first motor 155. In the same way, when the signal detector 132 detects the maximum strength of the signal generated by the grid position signal source generator 242, the processor 610 controls and stops the second motor 162.

The control signals to and from the PCBs 210 and 240 may be filtered by the LPF 615a-615d to remove high frequency noise signals from the analog measurement and to help remove aliased frequency components during analog-to-digital conversion. This limits the likelihood of a false positive.

When the field sensing device 130 is moved to the initial position by the first and second motors 155 and 162, the processor 610 activates only the grid position signal source generators of the first kind 242 and controls the second motor 162 to continuously move the field sensing device 130 toward the last predetermined position along the X-axis. When the signal detector 124 reports detection of the maximum signal strength to the processor 610, the processor 610 sends a control signal to the converter 144 to convert EM vectors sensed by the field sensing device 130 to digital samples.

In an aspect, when the field sensing device 130 only has one sensor, the field sensing device 130 may include a PCB, grid position signal source generators, and a third motor such as the PCB 210, the grid position signal source generator 212, and the first motor 155. The processor 610 stops the second motor 162, controls the third motor to continuously move the sensor along the Y-axis, and sends a control signal to the converter 144 when the processor 610 receives detection of the maximum strength of the signal generated by a grid position signal source generator located along the Y-axis. After the field sensing device 130 reaches the last predetermined position along the Y-axis, the processor 610 controls the second motor 162 to move the field sensing device 130 along the Z-axis.

In another aspect, when the field sensing device 130 includes a plurality of sensors 134, the processor 610 controls the second motor 162 to continuously move the field sensing device 130 along the X-axis. The field sensing device 130 sends all results sensed by the sensors 134 with the corresponding time stamp information to the converter 144. The converted results are transmitted to the computing device 148 via the CGS 146 and processed by the computing device 148. The converter 144 will not convert the sensed results unless it receives another control signal from the processor 610, while the sensors 134 continuously sense the EM vectors and sends to the converter 144. In an aspect, the CGS 146 may compute pickup values from the raw digitized data from the plurality of sensors 134 and compute position and orientation data from the pickup values. In another aspect, the computing device 148 may collate the pickup data or position and orientation data to create a mapping file or compute accuracy results.

For generating accuracy testing data, descriptions are mostly the same as those of generating the mapping data. In this situation, the processor 610 only activates the grid position signal source generators of the second kind 244 instead of the first kind 242.

In an aspect, the platform 110 and the carriage 120 may be made of non-ferrous materials and most of the field sensing device 130 may also be made of non-ferrous materials except the plurality of sensors 134. Further, the first motor 155 and the second motor 162, which include ferrous materials, may be distanced from the EM field generated by the EM field generator 195. By placing elements, which include ferrous materials, sufficiently far from the EM field, the system 100 can minimize influences to the EM field.

Figure 7A:
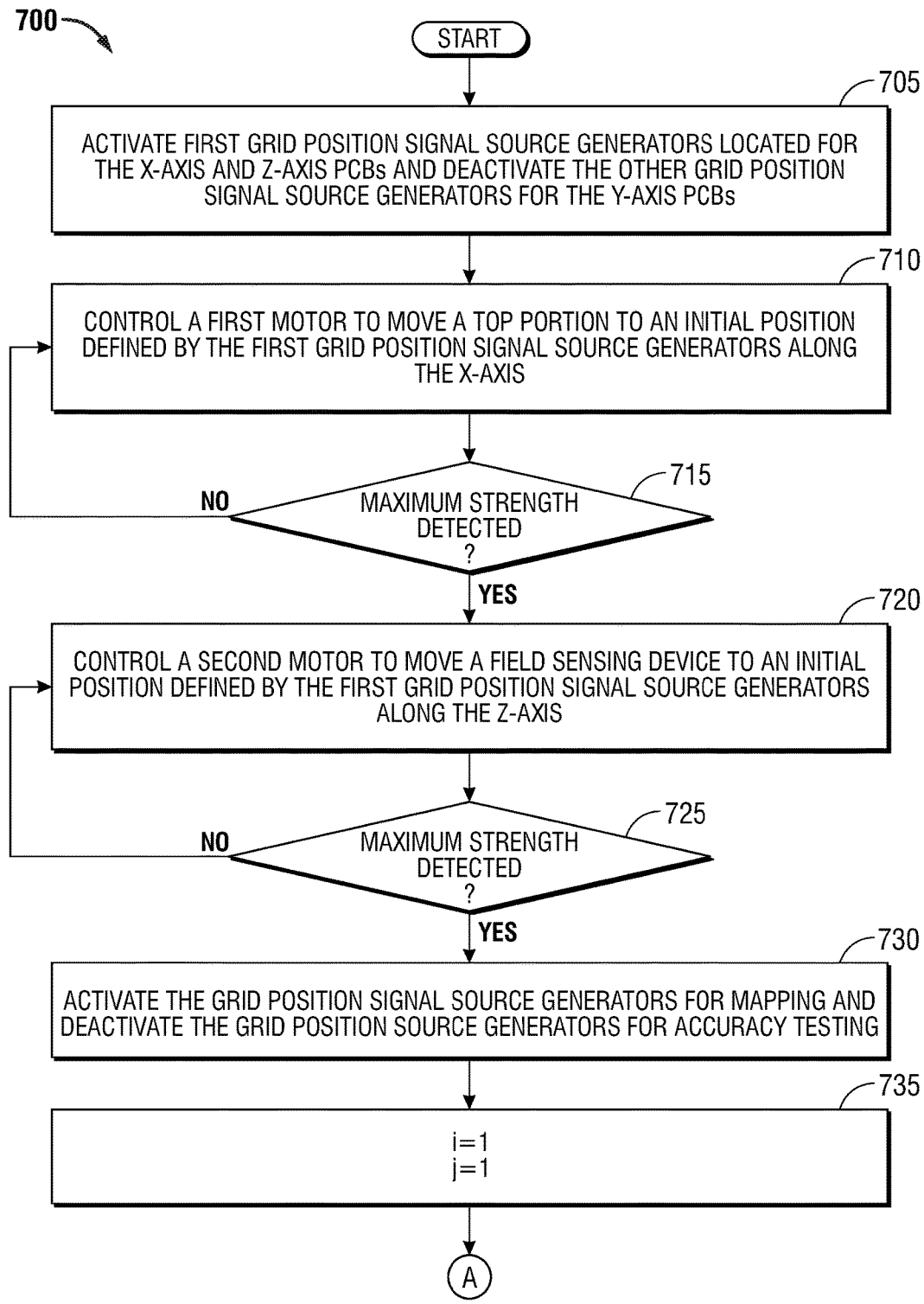
FIGS. 7A and 7B are flowcharts of a method for generating mapping data for an EMN system in accordance with an illustrative embodiment of the present disclosure.
Figure 7B:
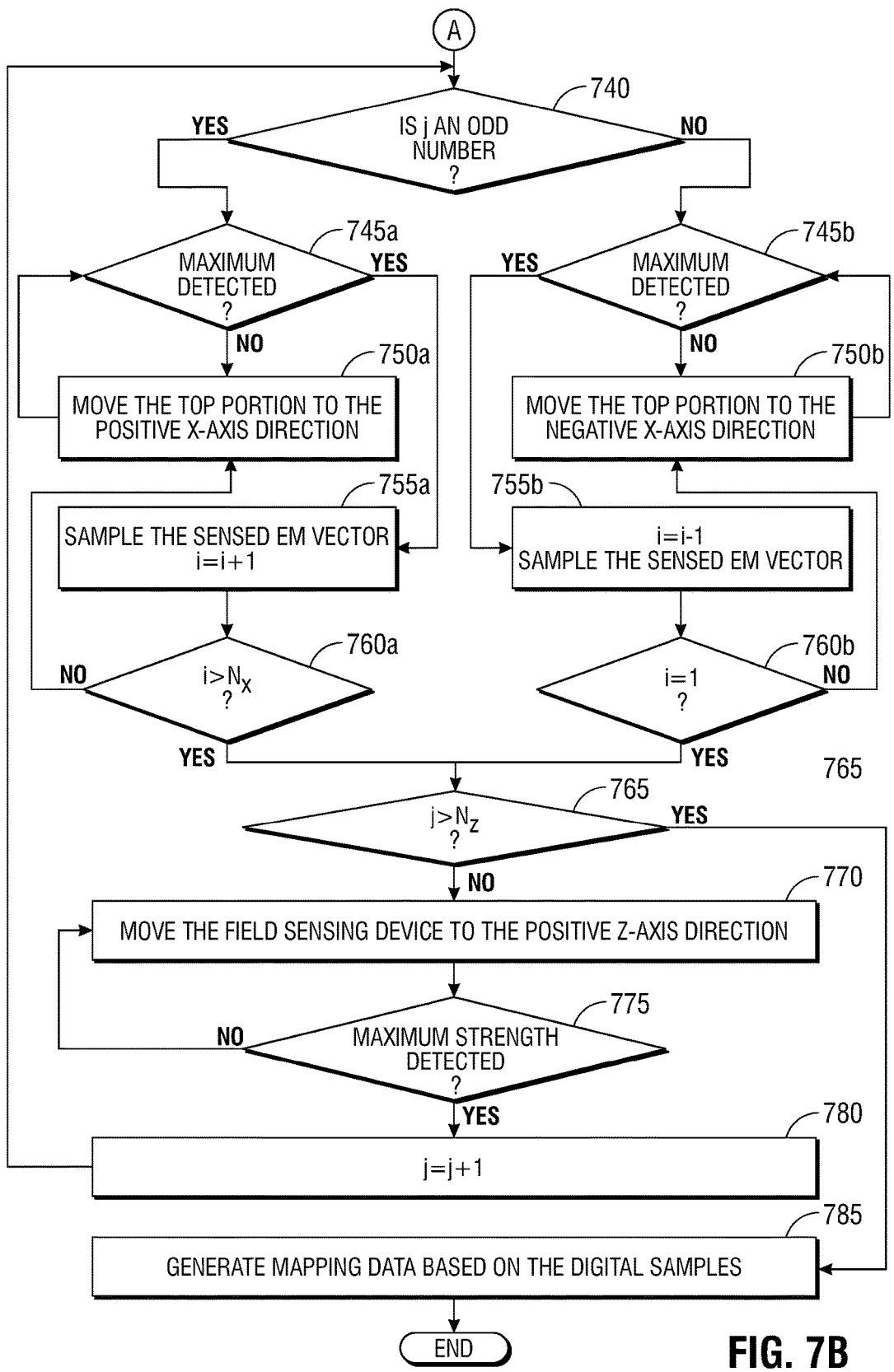

FIGS. 7A and 7B show a flow chart illustrating a method 700 for controlling the system 100 of FIG. 1 to generate mapping data for an EMN system. When the system 100 is powered and set for generating the mapping data, the first grid position signal source generator 212 positioned on the PCB 210 and the first grid position signal source generator 242 positioned on the PCB 240 are activated and the other grid position signal source generators are deactivated in step 705. By the first grid position signal source generators of the PCBs 210 and 240, an initial position for generating the mapping data is detected.

In step 710, the first motor 155 is controlled to move the carriage 120 to the initial position along the X-axis. At the same time, the signal detector 124 is continuously looking for and detecting strength of the signal generated by the first grid position signal source generator 212 of the PCB 210.

In step 715, it is determined whether the maximum strength is detected, where the maximum strength is predetermined (e.g., the maximum 325 as shown in FIG. 3) and the strength detected by the signal detector 124 is compared with the predetermined value. In a case when the maximum strength is not detected, the first motor 155 continuously moves the carriage 120 until the signal detector 124 detects the maximum strength.

When it is determined that the maximum strength is detected in step 715, the second motor 162 is controlled to move the field sensing device 130 to the initial position along the Z-axis. The signal detector 132 is continuously looking for and detecting strength of the signal generated by the first grid position signal source generator 242 of the PCB 240.

In step 725, it is determined whether the maximum strength is detected, where the maximum strength is predetermined (e.g., the maximum 325 as shown in FIG. 3) and the strength detected by the signal detector 132 is compared with the predetermined value. In a case when the maximum strength is not detected, the second motor 162 continuously moves the field sensing device 130 until the signal detector 132 detects the maximum strength. When it is determined that the maximum strength is detected in step 725, the field sensing device 130 and the carriage 120 are positioned on the initial position defined by the first grid position signal source generators of the PCBs 210 and 240. In an aspect, rather than being simply compared to a predetermined value, the field strength may be measured, and maximum determined by identifying a peak in the profile, which can be found at a point where the rate of change of the strength of the signal changes from positive to negative.

In an aspect, steps 710 and 715 may be performed after steps 720 and 725. In another aspect, steps 710 and 720 may be performed simultaneously and, likewise, steps 715 and 725 are performed simultaneously. That is, the carriage 120 and the field sensing device 130 may be moved independently and simultaneously by the first motor 155 and the second motor 162.

In step 730, the grid position signal source generators for mapping (i.e., the grid position signal source generators of the first kind 242) are activated and the grid position signal source generators for accuracy-testing (i.e., the grid position signal source generators of the second kind 244) are deactivated and, in step 735, the index "i" for the X-axis and the index "j" for the Z-axis are initialized to one.

In an aspect, the processor 610 communicates to the computing device 148 that the field sensing device 130 can start sensing EM vectors generated by the EM field generator 195. After the field sensing device 130 starts sensing the EM vectors, the computing device 148 informs the processor 610 that the field sensing device 130 senses the EM vectors, the converter 144 samples the sensed EM vectors, and the computing device 148 records the sampling data with corresponding time stamp information and the positional information.

FIG. 7B illustrates steps following step 735. After initialization of the indexes "i" and "j", it is determined whether the index "j" is an odd or even number in step 740. When it is determined that the index "j" is an odd number, it is determined whether the maximum strength is detected by the signal detector 124 in step 745a.

In the situation when the maximum strength is not detected, the first motor 155 is controlled to move the carriage 120 in the positive X-axis direction in step 750a and steps 745a and 750a are repeated until the maximum strength is detected.

When it is determined that the maximum strength is detected in step 745a, the processor 610 sends a control signal to the converter 144 via the computing device 148 so that the converter 144 receives and digitally samples the sensed EM vectors in step 755a. The digital samples include positional information indicating a current position at which each sensor 134 of the field sensing device 130 is located. After the control circuitry 170 sends the positional information to the CGS 146 and the computing device 148, the index "i" of the X-axis is incremented by one in step 755a.

In an aspect, the field sensing device 130 continuously senses EM vectors so that, when a refined resolution of the EM field is needed, simply increasing a number of grid position signal source generators in any direction can result in a higher resolution of the mapping data.

In step 760a, the index "i" is compared with the predetermined number $N_x$, which is a predetermined number of the grid position signal source generators for mapping data along the X-axis. When the index "i" is not greater than (i.e., less than or equal to) a predetermined number $N_x$, steps 745a-760a are performed until the index "i" is greater than the predetermined number $N_x$. When the index "i" is greater than the predetermined number $N_x$ that indicates the EM vectors have been sampled at all predetermined positions along the X-axis.

In an aspect, the predetermined number $N_x$ may be less than the number of the grid position signal source generators positioned on the PCB 210 by one or two. The first and/or last grid position signal source generator may be used to indicate the starting and/or ending position, respectively, and not used for sensing the EM vectors. In another aspect, the predetermined number $N_x$ may be equal to the number of the grid position signal source generators positioned on the PCB 210.

When it is determined that the index "i" is greater than the predetermined number $N_x$ in step 760a, the next comparison is to determine whether the index "j" is equal to the predetermined number $N_z$ in step 765. When it is determined that the index "j" is not equal to the predetermined number $N_z$, the second motor 162 moves the field sensing device 130 to the positive Z-axis in step 770.

In step 775, it is determined whether the maximum strength is detected. If the maximum strength is not detected, the second motor 162 keeps moving the field sensing device 130 to the positive Z-axis. When it is determined that the maximum strength is detected in step 775, the index "j" of the Z-axis is increased by one in step 780 and the process returns to step 740. This changes the oddness of the index (i.e., changing an odd number to an even number and vice versa).

In step 765, when the index "j" is determined to be equal to the predetermined number $N_z$ the process proceeds to step 785 where mapping data based on the digital samples is generated, as described in greater detail below. Otherwise, steps 740-780 are performed until the index "j" is equal to the predetermined number $N_z$.

Referring back to step 740, when the index "j" is determined not greater than the predetermined number $N_z$, the index "j" becomes an even number so that the method 700 follows steps 745b-760b. Descriptions for step 745b are the same as those of step 745a.

In step 750b, the first motor 155 is controlled to move the carriage 120 to the negative X-axis direction. As described in steps 750a, step 750b is performed until the maximum strength is detected.

When the maximum strength is detected in step 745b, the index "i" is decremented by one and the converter samples the sensed EM vectors in step 755b. By first decrementing the index "i", the index "i" corresponds to the current position of the field sensing device 130 along the X-axis.

In step 760b, the index "i" is compared with one. When it is determined that the index "i" is not equal to one, steps 745b-760b are repeated. Otherwise, step 765 follows and descriptions for following steps are the same as described above.

By using oddity of the index "j" (i.e., steps 745a-760a and steps 745b-760b), the carriage 120 does not have to move back to the initial position after scanning through each line of predetermined positions along the X-axis.

When the index "j" is determined equal to the predetermined number $N_z$ in step 765, mapping data is generated based on the EM vectors sensed at the predetermined positions in step 785. Each of the EM vectors includes strength of the EM field at a predetermined position defined by three coordinates (e.g., (x, y, z)). The first coordinate is defined by the index "i," the third coordinate is defined by the index "j," and the second coordinate is defined by the location of the sensor 134 of the field sensing device 130 along the Y-axis. Further, time stamp information is included in the EM vector.

In an aspect, the mapping data may include equations of fitted curves similar to the fitted curve 310 of FIG. 3. The fitted curve equations may be polynomial function based or harmonic function based. When the EMN system maps internal organs of a patient using the mapping data, the locations of the internal organs are determined based on the fitted curve and measured strength of the EM field.

Figure 8A:
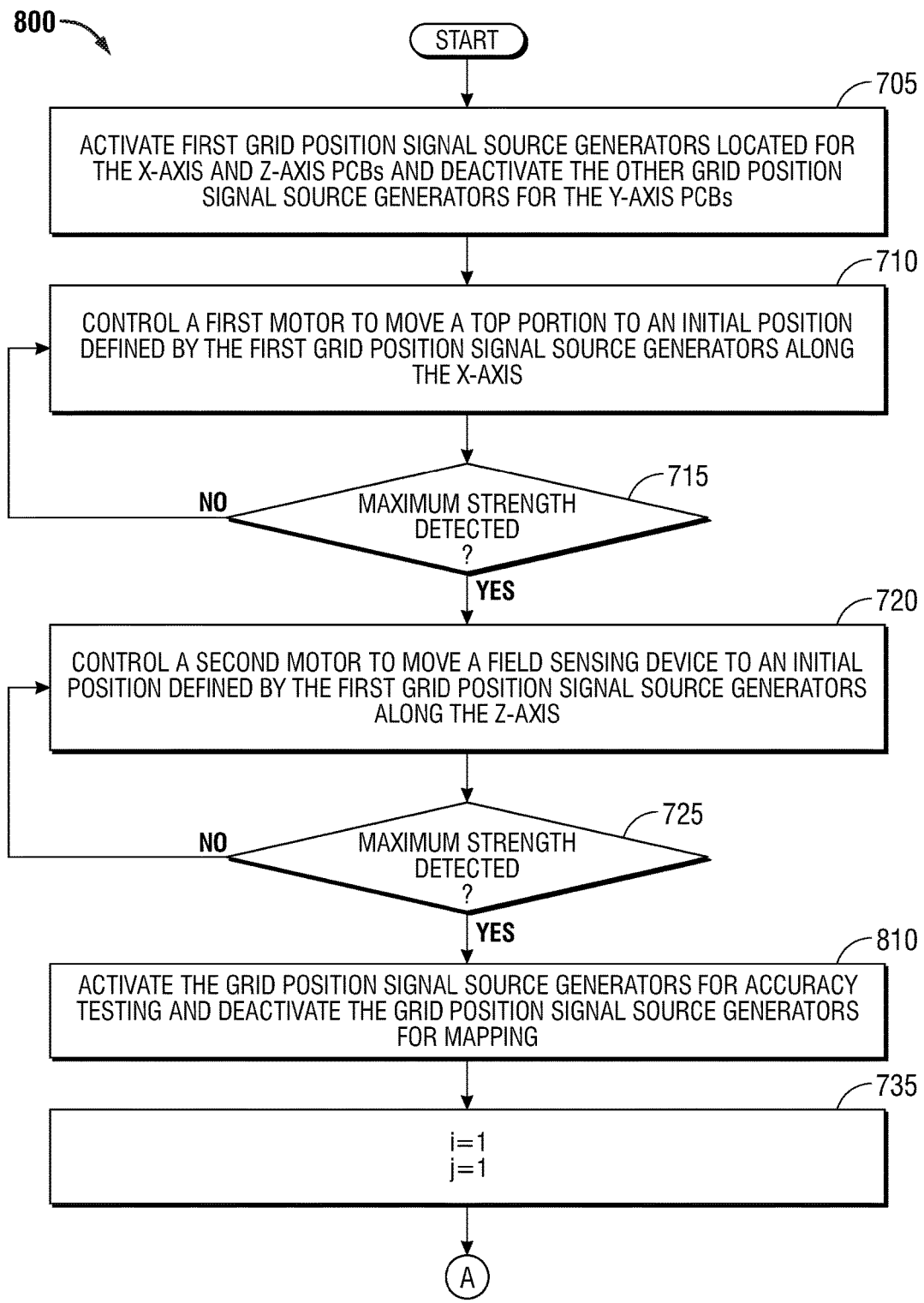
FIGS. 8A-8C are flowcharts of a method for testing accuracy of the mapping data in accordance with an illustrative embodiment of the present disclosure.
Figure 8B:
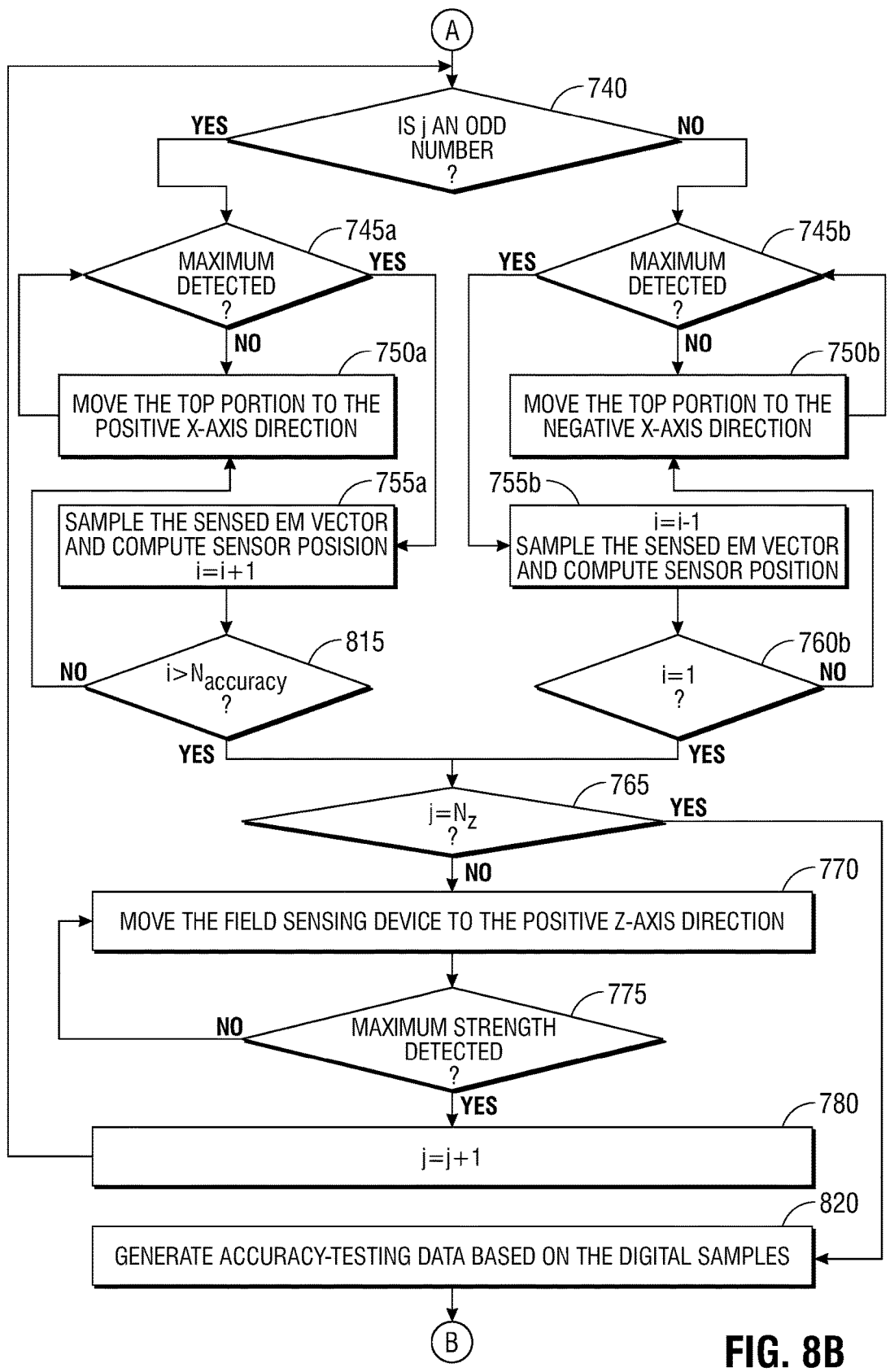
Figure 8C:
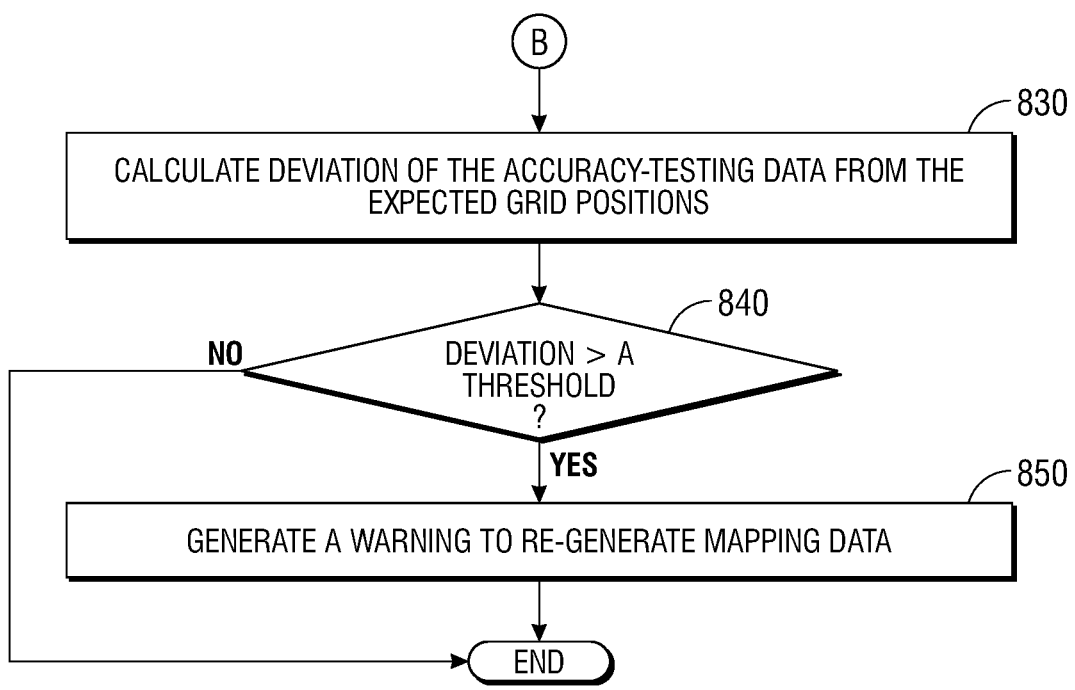

FIGS. 8A-8C show flow charts illustrating a method 800 for testing accuracy of the mapping data in accordance with embodiments of the present disclosure. FIGS. 8A-8C include steps which are similar to steps as described above with reference to FIGS. 7A and 7B and thus their description is omitted here. In FIG. 8A step 810 replaces step 730 and in FIG. 8B step 815 replaces step 760a. As depicted in FIG. 8A, when the maximum strength is detected in step 725, the grid position signal source generators for accuracy testing are activated and the grid position signal source generators for mapping are deactivated in step 810. With respect to FIG. 8B, the predetermined number $N_{accuracy}$ for generating accuracy-testing data may be different than the predetermined number $N_x$ for generating mapping data described with respect to FIG. 7B. The description for step 815 is similar to that for step 760a by replacing the predetermined number $N_x$ with predetermined number $N_{accuracy}$. Thus, when it is determined that the index "i" is greater than $N_{accuracy}$ the process proceeds to step 765.

When it is determined that the index "j" is equal to $N_z$ in step 765, accuracy-testing data is generated based on the digital samples in step 820. The generated accuracy-testing data is compared with the fitted curves stored in the computing device. Specifically, expected values are calculated based on the fitted curves at the locations of the grid position signal source generators of the second kind 244. Since the grid position signal source generators of the second kind 244 are located between two consecutive grid position signal source generators of the first kind 242, accuracy-testing data at a predetermined position for accuracy-testing should be bounded by the corresponding two expected values and within an acceptable tolerance range from the fitted curve.

In an aspect, a fitted curve is generated along the Z-axis when x and y coordinates fixed as shown in FIG. 3. Based on the fitted curve 310, expected values may be calculated based on the position of the predetermined positions, such as values indicated by the dotted lines. These expected values are compared with the accuracy-testing data and a deviation error is calculated based on the difference between the expected values and the accuracy-testing data in step 830. The deviation error may be standard deviation, root mean square, or other statistically meaningful value which a person having ordinary skill in the art would readily appreciate.

In step 840, the deviation error is compared with a predetermined threshold. If the deviation error is less than or equal to the predetermined threshold, the mapping data is deemed to be sufficiently accurate and the method 800 is ended.

If it is determined that the deviation error is greater than the predetermined threshold in step 840, the mapping data is deemed to be inaccurate and, in step 850, a warning is generated to inform the user of the EMN system that the mapping data needs to be re-generated. In an aspect, the warning may be displayed on a screen of the system 100 or may be an audio to inform such. The warning may be any other means, such as light, means to automatically disable the EMN system, etc., without departing from the scope of the present disclosure.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure.

What is claimed is:

1. An apparatus for mapping and accuracy-testing an electromagnetic (EM) navigation system, comprising:
   a sensor configured to sense EM vectors of an EM field generated by the EM navigation system;
   a carriage configured to move the sensor along a first direction and a second direction different from the first direction;
   a first position detector operatively associated with the sensor and configured to detect a first position of the sensor along the first direction, where the first position is one of predetermined positions along the first direction;
   a second position detector operatively associated with the sensor and configured to detect a second position of the sensor along the second direction, wherein the second position is one of predetermined positions along the second direction; and
   a controller operatively associated with the sensor and configured to control movements of the carriage along the first and second directions and map the EM field based on the sensed EM vectors at predetermined positions in a coordinate system defined by the first direction, the second direction, and a third direction perpendicular to a plane defined by the first and second directions,
   wherein the predetermined positions along the second direction include a first group, and
   wherein the sensor is configured to sense an EM vector for mapping at each position of the first group of the predetermined positions along the second direction.

2. The apparatus according to claim 1, further comprising a plurality of signal generators each of which being configured to generate a signal, and each of which being positioned at a corresponding position of the predetermined positions along the first direction.

3. The apparatus according to claim 1, wherein the predetermined positions along the second direction further include a second group, and
   wherein the sensor is configured to sense an EM vector for accuracy-testing at the second group of the predetermined positions along the second direction.

4. The apparatus according to claim 3, further comprising:
   a first plurality of signal generators each being configured to generate a signal, and each of which is positioned at a corresponding position of the first group; and
   a second plurality of signal generators each being configured to generate a signal, and each of which is positioned at a corresponding position of the second group.

5. The apparatus according to claim 1, wherein the sensor includes an EM sensor configured to sense an EM vector along the third direction, and wherein the EM sensor is configured to be manually moved along the third direction.

6. The apparatus according to claim 1, wherein the sensor includes a plurality of sensors, each of which is located at corresponding one of predetermined positions along the third direction.

7. The apparatus according to claim 1, further comprising a bottom layer configured to center the apparatus over an EM field generated by the EM navigation system.

8. The apparatus according to claim 1, wherein the apparatus is mostly made of non-ferrous materials.

9. The apparatus according to claim 1, further comprising:
   a first motor coupled with the sensor via a first shaft and configured to move the sensor along the first direction; and
   a second motor coupled with the sensor via a second shaft and configured to move the sensor along the second direction.

10. The apparatus according to claim 1, wherein the sensed EM vectors include time stamp information.

11. A method for mapping and accuracy-testing an electromagnetic (EM) field generated by an EM navigation system, comprising:
    moving a sensor to an initial position on a plane defined by a first direction and a second direction different from the first direction;
    sensing an EM vector at each of predetermined positions in a coordinate system defined by the plane and a third direction perpendicular to the plane;
    sampling the sensed EM vector to obtain digital samples;
    generating data for mapping or accuracy-testing based on the digital samples;
    generating a fitted curve of the mapping data based on the digital samples; and
    storing the fitted curve in the EM navigation system,
    wherein the predetermined positions are defined by first predetermined positions along the first direction, second predetermined positions along the second direction, and third predetermined positions along the third direction, and
    wherein a signal generator is located at each of the third predetermined positions, and wherein the method further comprises:
    moving the sensor along the third direction; and
    sensing an EM vector when a strength of a signal generated by a signal generator is a maximum.

12. The method according to claim 11, further comprising:
    generating accuracy-testing data;
    calculating deviation of the accuracy-testing data from the fitted curve;
    determining whether the deviation is greater than a threshold; and
    generating a warning of re-generating the mapping data when it is determined that the deviation is not less than the threshold.

13. The method according to claim 11, wherein the second predetermined position includes a first group of positions for mapping and a second group of positions for accuracy-testing, wherein signal generators located at the first group are configured to generate signals for mapping, and wherein signal generators located at the second group are configured to generate signals for accuracy-testing.

14. A method for mapping and accuracy-testing an electromagnetic (EM) field generated by an EM navigation system, comprising:
    moving a sensor to an initial position on a plane defined by a first direction and a second direction different from the first direction;

sensing an EM vector at each of predetermined positions in a coordinate system defined by the plane and a third direction perpendicular to the plane;

sampling the sensed EM vector to obtain digital samples;

generating data for mapping or accuracy-testing based on the digital samples;

generating a fitted curve of the mapping data based on the digital samples; and storing the fitted curve in the EM navigation system, wherein the predetermined positions are defined by first predetermined positions along the first direction, second predetermined positions along the second direction, and third predetermined positions along the third direction, and wherein the sensor includes EM sensors, each of which is located at a corresponding position of the third predetermined positions.

15. The method according to claim 11, wherein the step of moving the sensor to the initial position includes:

activating a first signal generator located at a beginning position of the first predetermined positions and a second signal generator located at a beginning position of the second predetermined positions; and moving the sensor to a position where the sensed strength is a maximum along the first and second directions.

16. The method according to claim 12, wherein the generated warning is a screen, an audio, or light.

* * * * *